US00PP09462P

United States Patent [19]

Hofstede et al.

[11] Patent Number: Plant 9,462

[45] Date of Patent: Mar. 5, 1996

[54] HYDRANGEA PLANT NAMED 'HOBELLA'

[76] Inventors: J. G. Hofstede; W. J. G. Hofstede, both of Doormanstraat 6, 6852 AK Huissen, Netherlands

[21] Appl. No.: 399,471

[22] Filed: Mar. 7, 1995

[51] Int. Cl.[6] ..... A01H 5/00

[52] U.S. Cl. ..... Plt./67.1

[58] Field of Search ..... Plt./67.1

*Primary Examiner*—James R. Feyrer

*Attorney, Agent, or Firm*—Christie, Parker & Hale

[57] ABSTRACT

A new variety of *Hydrangea macrophylla* 'Hobella' producing clusters of flowers that pass through three phases of different coloration.

2 Drawing Sheets

BACKGROUND OF THE INVENTION

The present invention relates to a new and distinct variety of *Hydrangea macrophylla* which was originated as a selected seedling derived by crossing as seed and pollen parents two undistributed, unnamed seedlings of my creation identified as 'K731' and 'W734', respectively. The varietal denomination of this new plant is 'Hobella'.

SUMMARY OF THE INVENTION

The new variety produces large, soft pink flowers which when just blooming are in lace cap form. Subsequently, more sterile flowers appear between the fertile flowers in the center which give the impression of a flower head with only sterile flowers, which of course depends upon on the bud development. When placed in front of a window, the soft pink color becomes lemon green and when the plant is placed outside, the lemon green becomes cherry red. This color change is refer to as three phases of colorization; namely, phases 1, 2 and 3, respectively.

The new variety has been asexually reproduced vegetatively from cuttings and the first asexual reproduction of 'Hobella' was accomplished by vegetative cuttings in a controlled environment in Huissen, Gelderland Province, in The Netherlands.

BRIEF DESCRIPTION OF THE ILLUSTRATIONS

The accompanying photographic illustrations show typical plant specimens of the new cultivar with colors as true as possible for color illustrations of this type.

FIGS. 1, 2 and 3 illustrate the change in coloration occurring through the three phases of color change characteristic of this variety.

DETAILED DESCRIPTION

Parentage

Figure 1:
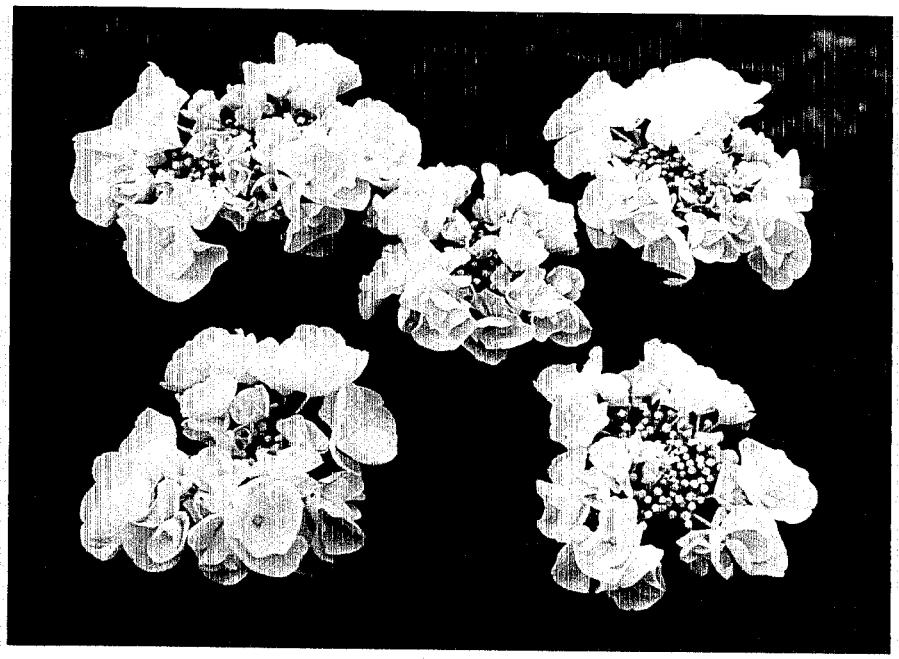
Figure 2:
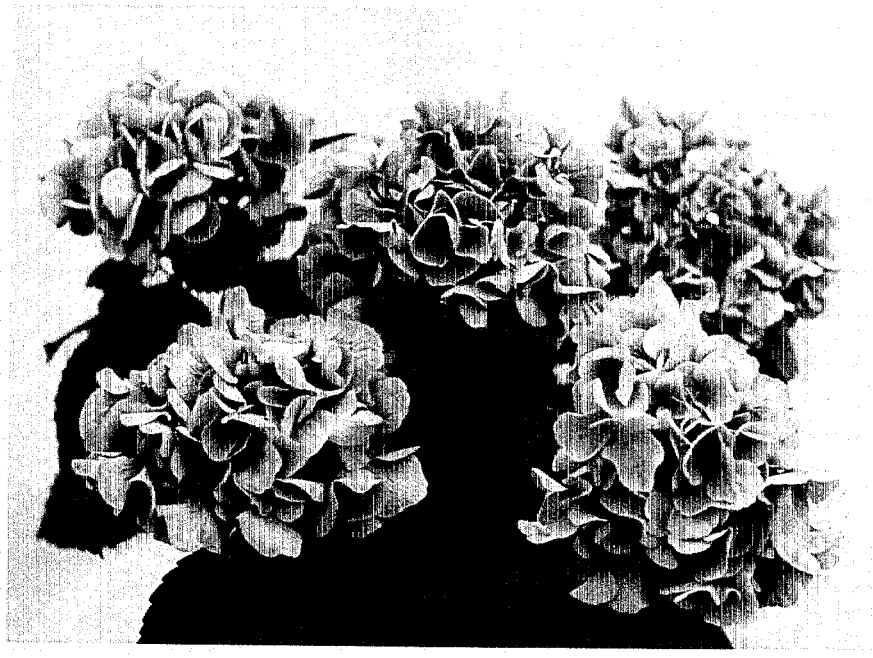
Figure 3:
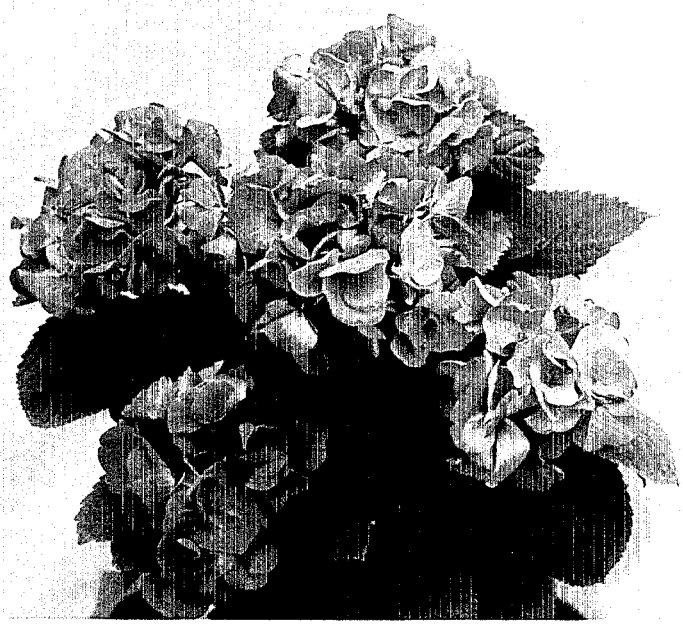

*Seed parent.*—K731'.

*Pollen parent.*—W734'.

*Classification.*—*Hydrangea macrophylla* 'Hobella'.

The following is a detailed description of the new variety with color designations in accordance with The Royal Horticultural Society Colour Chart. Observations provided are of specimens grown under glass in Gelderland, the Netherlands in November and color observations are made of specimens grown outdoors in Angers, France, in August and September.

Flower

A. Blooming habit: The entire inflorescence (fertile and sterile) is flat.

B. Bud:
- (1) *Size.*—medium and small.
- (2) *Form (shape).*—side view — cylindrical to columnar; front view—conical, elongated.
- (3) *Color.*—green-red.
- (4) *Rate of opening.*—Normally closed.
- (5) *Peduncle length.*—About 3 cm. Strength: Erect, strong. Color: 51D.
- (6) *Distinguishing characteristics.*—The total habitus of florescence and coloration change.

C. Flower description:
- (1) *Flower head.*—obconical.
- (2) *Size (average size when fully open).*—About 16 to 22 cm.
- (3) *Flower cluster.*—About 8×12 cm.
- (4) *Petalage (number of petals under normal conditions).*—4.
- (5) *Colors.*—Phase 1: pink petals near 62D to near 69A, near 75D and 73C and 73D; Phase 2: green petals inside near 144B, outside near 138C; Phase 3: red petals near 60A, 59B, 53A and 46A; with some green parts near 144B and 138C.
- (6) *Blooming period.*—Outdoor: July–September. Greenhouse: early March–November.
- (7) *Petals.*—Texture: average for hydrangea. Appearance: inside velvety; outside silky.
- (8) *Form.*—Heart-shaped like leaf of *Ginkgo biloba.*
- (9) *Fragrance.*—No.
- (10) *Lasting quality on plant.*—On plant: pink 4–6 weeks, green 3–8 weeks, red 4–8 weeks.
- (11) *Distinguished characteristics.*—Change of flower coloration with time.

PLANT

A. Habit: Upright, not very compact.

B. Growth: Similar to other *H. macrophylla.*

C. Height attained (first season): About 20 cm (nominal).

D. Width: About 15 cm (nominal).

E. Foliage (fully mature):
- (1) *Width.*—Strong branch — about 10 to 13 cm; Small branch — about 8 cm.
- (2) *Length.*—Strong branch — about 14 to 16 cm; Small branch — about 10 to 11 cm.
- (3) *Quantity.*—3 to 4 pairs per branch.
- (4) *Color.*—Upper side: near 136A; Underside: near 138B.
- (5) *Shape.*—elliptic.

(6) *Texture.*—Upper side: flat and dull; Underside: matte.

(7) *Margin.*—serrated.

(8) *Serration.*—Serrate.

(9) *Stems.*—Few black points (lenticels).

(10) *Ribs and veins.*—present.

(11) *Petioles (length).*—About 2 to 2.5 cm.

F. Wood (1) *New shoots.*—Color: near 145B; Bark: smooth.

(2) *Old wood.*—Color: 200A (dark); 164A and 165B (light); Bark: smooth.

E. Winter hardiness: In Spring when buds start to grow, young leaves need protection from Spring frost.

What is claimed is:

1. A new and distinct variety of Hydrangea plant substantially as shown and described, characterized by changing flower coloration.

* * * * *

UNITED STATES PATENT AND TRADEMARK OFFICE

CERTIFICATE OF CORRECTION

PATENT NO. : Plant 9,462

DATED : March 5, 1996

INVENTOR(S) : J.G. Hofstede; W.J.G. Hofstede

It is certified that error appears in the above-indentified patent and that said Letters Patent is hereby corrected as shown below:

Column 1, line 42, change "K731'" to -- 'K731' --.
Column 1, line 43, change "W734'" to -- 'W734' --.
Column 2, line 5, after "medium" change "and" to -- to --.

Signed and Sealed this

Tenth Day of September, 1996

*Attest:*

Bruce Lehman

BRUCE LEHMAN

*Attesting Officer*

*Commissioner of Patents and Trademarks*